United States Patent [19]

Kelley

[11] 4,031,909

[45] June 28, 1977

[54] DENTAL FLOSS HOLDER AND DISPENSER

[75] Inventor: John J. Kelley, Harwinton, Conn.

[73] Assignee: The Raymond Lee Organization, Inc., a part interest

[22] Filed: May 25, 1976

[21] Appl. No.: 689,731

[52] U.S. Cl. .............................................. 132/91
[51] Int. Cl.² ........................................ A61C 15/00
[58] Field of Search ................... 132/91, 89, 92 R

[56] References Cited

UNITED STATES PATENTS

| 754,841 | 3/1904 | Bessonet | 132/92 A |
|---|---|---|---|
| 1,161,043 | 11/1915 | Gallas | 132/92 A |
| 2,517,806 | 8/1950 | Streiler | 132/91 |
| 3,853,134 | 12/1974 | McCord | 132/92 A |

Primary Examiner—G.E. McNeill

[57] ABSTRACT

A forked member has a shank with two spaced outwardly disposed prongs at one end. These prongs have outer surfaces with longitudinally extending grooves and tips with transversely disposed aligned bores essentially coplanar with the grooves. A longitudinally disposed sleeve is secured at one end to the other end of the shank. The sleeve has a first conically shaped hollow bore extending longitudinally through the sleeve between the ends. The apex of the bore is disposed at one end of the sleeve. The sleeve has a second bore extending transversely from the outside surface to the apex. A floss cutter is secured to the shank adjacent its other end. A hollow container with floss therein detachably engages the sleeve. The floss passes through the first and second bores, along the grooves and through the aligned bores of the prongs and terminates at the cutter. A manually adjustable device secured to the shank intermediate its ends detachably engages the floss both before it reaches the prongs and after it leaves the prongs to draw taut that portion of the floss which extends between the aligned bores in the prongs.

3 Claims, 4 Drawing Figures

DENTAL FLOSS HOLDER AND DISPENSER

SUMMARY OF THE INVENTION

This invention is directed toward a dental floss holder and floss dispenser that can be manufactured easily and inexpensively and that can be easily and effectively used.

To this end, a forked member has a shank with two spaced outwardly disposed prongs at one end. These prongs have outer surfaces with longitudinally extending grooves and tips with transversely disposed aligned bores essentially coplaner with the grooves. A longitudinally disposed sleeve is secured at one end to the other end of the shank. The sleeve has a first conically shaped hollow bore extending longitudinally through the sleeve between its ends. The apex of the bore is disposed at one end of the sleeve. The sleeve has a second bore extending transversely from the outside surface to the apex. A floss cutter is secured to the shank adjacent its other end. A hollow container with floss therein detachably engages the sleeve. The floss passes through the first and second bores, along the grooves and through the aligned bores of the prongs and terminates at the cutter. A manually adjustable device secured to the shank intermediate its ends detachably engages the floss both before it reaches the prongs and after it leaves the prongs to draw taut that portion of the flow which extends between the aligned bores in the prongs.

The user, holding the invention in hand, uses the taut portion of the floss to clean spaces between adjacent teeth in conventional manner. The device can be loosened to enable lengths of floss to be cut away as desired and can be tightened to draw the floss taut as previously described.

DETAILED DESCRIPTION OF PREFERRED EMBODIMENT

Figure 1:
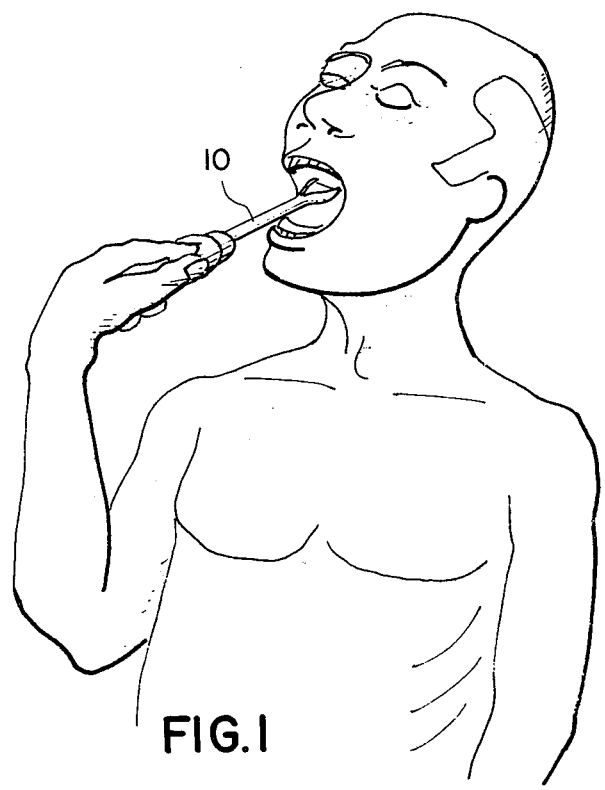
FIG. 1 shows the invention in use.
Figure 3:
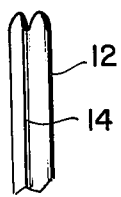
FIG. 3 is a view taken along line 3—3 in FIG. 2.
Figure 4:
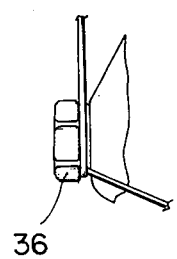
FIG. 4 is an enlarged detail view of a portion of the structure shown in FIG. 3.
Figure 2:
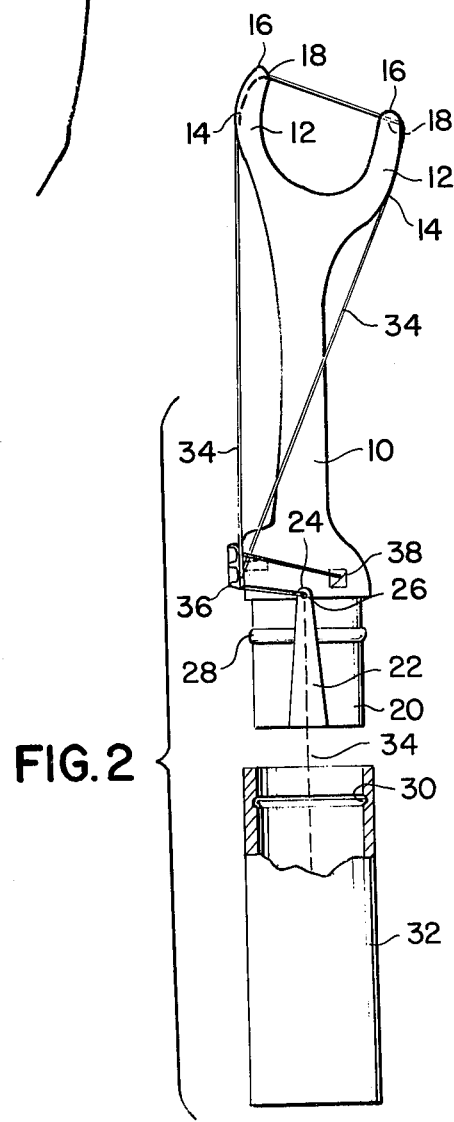
FIG. 2 is an exploded view of the invention.

Referring now to FIGS. 1-4, a forked member has a shank 10 with two spaced outwardly disposed prongs 12 at one end. These prongs have outer surfaces with longitudinally extending grooves 14 and tips 16 with aligned transverse bores 18 essentially in a common plane with the grooves.

A longitudinally disposed sleeve 20 is secured to the opposite end of shank 10. Sleeve 20 has a conical bore 22 extending longitudinally through the sleeve with apex 24 disposed at the opposite end of the shank. A bore 26 extends transversely from the apex to the outer surface of the shank. The shank has an outer circular ridge 29 which snap fits into circular groove 30 in the open end of hollow cylindrical member 32. Member 32 contains a removable roll of dental floss, with the floss 34 extending through bore 22, bore 24, around fixed binder button 36 secured to the side of shank 10, upward through one groove 14, through aligned bores 18, through the other groove 14, back between the button and shank and finally to cutter 38.

The button enables the floss to be drawn taut or to be loosened to enable a section of floss to be cut off.

I claim:
1. A dental floss holder and dispenser comprising:
a forked member having a shank with two spaced outwardly disposed prongs at one end, said prongs having outer surfaces with longitudinally extending grooves and tips with transversely disposed aligned bores essentially coplanar with the grooves;
a longitudinally disposed sleeve secured at one end to the other end of the shank, said sleeve having a first conically shaped hollow bore extending longitudinally through the sleeve between its ends, the apex of the bore being disposed at one end of the sleeve, said sleeve having a second bore extending transversely from the outside surface to said apex;
a floss cutter secured to said shank adjacent said other end;
a hollow container with floss therein detachably engaging the sleeve, said floss passing through said first and second bores, along said grooves, through the aligned bores of the prongs and terminating at the cutter; and
manually vertically adjustable slidable means secured to said shank intermediate its ends for detachably engaging the floss before it reaches the prongs and after it leaves the prongs to draw taut that portion of the floss which extends between the aligned bores in the prongs.

2. The holder of claim 1 wherein the hollow container is a cylinder open at one end, said open end of the cylinder and other end of the sleeve having mating manually engagable and disengagable means.

3. The holder of claim 2 wherein said adjustable means includes a fixed binder button.

* * * * *